United States Patent
Lerche et al.

(10) Patent No.: US 6,691,057 B2
(45) Date of Patent: Feb. 10, 2004

(54) METHOD AND DEVICE FOR ACCELERATED STABILITY ANALYSIS

(75) Inventors: Dietmar Lerche, Berlin (DE); Volker Berwald, Berlin (DE)

(73) Assignee: L.U.M. Gesellschaft fur Labor-Umweltdiagnostic & Medizintechnik mbH, Berlin (DE)

( * ) Notice: Subject to any disclaimer, the term of this patent is extended or adjusted under 35 U.S.C. 154(b) by 89 days.

(21) Appl. No.: 10/079,812

(22) Filed: Feb. 22, 2002

(65) Prior Publication Data

US 2002/0147563 A1 Oct. 10, 2002

(51) Int. Cl.$^7$ .................. G01N 15/04; G01N 21/01
(52) U.S. Cl. .................. 702/127; 210/651; 356/450
(58) Field of Search ............... 702/127; 210/708, 210/651; 250/241.1, 241.8; 356/450; 359/370

(56) References Cited

U.S. PATENT DOCUMENTS

| | | |
|---|---|---|
| 4,099,871 A | 7/1978 | Sunahara et al. |
| 4,457,624 A | 7/1984 | Goldberg et al. |
| 5,783,826 A | 7/1998 | Meunier |

FOREIGN PATENT DOCUMENTS

| | | |
|---|---|---|
| AT | 397159 B | 2/1994 |
| DD | 216 104 A1 | 11/1984 |
| DE | 3618707 A1 | 12/1986 |
| DE | 3609552 | 8/1987 |
| DE | 4116313 C2 | 11/1998 |
| EP | 0760092 B1 | 2/1998 |
| JP | 05-078236 | 3/1993 |

OTHER PUBLICATIONS www.IFAC.de.

*Primary Examiner*—Kamini Shah
(74) *Attorney, Agent, or Firm*—Burns, Doane, Swecker & Mathis, LLP

(57) ABSTRACT

The invention relates to methods and devices for accelerated stability analysis, and in particular to a qualitative and quantitative direct estimation/identification of separation processes of disperse material systems (such as liquid-solid, liquid-liquid or liquid-gaseous). The invention also relates to methods and devices for the classification and quantitative characterization of slow, as well as rapid separation phenomena of disperse material systems of different volume concentration. Exemplary fields of application concern the development, selection and optimization of destabilizers, stabilizers and novel formulations for dispersions, as well as quality and process control (such as in the chemical, pharmaceutical, biotechnological, cosmetic and food industries), as well as in the process technology for separation and treatment processes.

38 Claims, 3 Drawing Sheets

|section A-A|

METHOD AND DEVICE FOR ACCELERATED STABILITY ANALYSIS

BACKGROUND OF THE INVENTION

1. Field of the Invention

The invention relates to methods and devices for accelerated stability analysis, and in particular to a qualitative and quantitative direct estimation/identification of separation processes of disperse material systems (such as liquid-solid, liquid-liquid or liquid-gaseous). The invention also relates to methods and devices for the classification and quantitative characterization of slow, as well as rapid separation phenomena of disperse material systems of different volume concentration. Exemplary fields of application concern the development, selection and optimization of destabilizers, stabilizers and novel formulations for dispersions, as well as quality and process control (such as in the chemical, pharmaceutical, biotechnological, cosmetic and food industries), as well as in the process technology for separation and treatment processes.

2. Background Information

In general, a differentiation can be made between indirect and direct methods for assessing the velocity of separation phenomena of dispersions and to the prediction of stability.

Indirect methods have in common that by various analytical methods, one or more material or dispersion parameters can be determined which influence the separation behavior on the basis of known basic physical law (Stokes' law), such as density, size distribution of the dispersed particles or the rheological behavior. However, Stokes' law has been derived under ideal conditions (e.g. extreme dilution). Hence, for complex, concentrated material systems, separation velocity cannot be calculated a priori and stability cannot be predicted without additional reference measurements, even with extensive determination of several relevant parameters.

Direct methods (e.g., centrifuge separation, gravitation separation and so forth) determine the separation velocity via the change of local composition of the dispersion in dependence of time. For example, it is known to use normal or analytical centrifuges with highly stable dispersions (very slow separation). See German Patent No. DE 4116313.3-52 which is hereby incorporated by reference in its entirety. In this case, separation is strongly accelerated. Aside from a series of measurement-technical problems (addressed, for example, using light transmission), rapidly separating dispersions cannot be accurately examined therewith. Moreover, the resulting centrifugal forces can lead to a change in the dispersion structure. A transfer to normal storage conditions is therewith not given.

Rapidly separating dispersions allow for assessment in a gravitational field. When particles have migrated over a sufficient path due to the force of gravitation, then corresponding concentration changes can be detected. A so-called test-tube test as per DIN 51599 is known. Here, the level of the clear phase is visually read after a determined time. The results, however, are subjective and have a preciseness on the order of, for example, 0.5 mm. For minimal documentation during this proceeding, images are in some cases generated by photographic or digital cameras, and are correspondingly stored in archives. A method is also known, wherein the information of the images is subsequently quantified by image processing (e.g., the Demulsibility Tester, produced by Analis, of Belgium). However, the method accords relatively low local and temporal resolution, the results depend on the absorption properties of the disperse and fluid phase (e.g., use of white light), large original data amounts to be administered, and there is reduced ability to accelerate the separation process.

Known methods for the analysis of separations include recording the occurring concentration or structural changes at predetermined locations of the dispersion sample using suitable measurement sensors. For example, electrodes are used for determining the conductivity (e.g., apparatus available from IFAC GmbH) of conductive dispersions. See, for example, www.IFAC.de, as are optical detectors (see, for example, Japanese Patent No. 5078236, U.S. Pat. Nos. 4,099,871, 4,457,624, German Patent No. DD 216104, and German Patent No. DE-OS 3618707, the disclosures of which are all hereby incorporated by reference in their entireties). With these methods, the position of the sensors is process-technically fixed, and hence, data on the dispersion areas between these sensors is not available. This can restrict the assessment of separation processes of complex dispersions.

Scanning sensor systems (e.g. scanning sedimentometers) are also used (See for example, German Patent No. DE 3609552, Austrian Patent No. AT 397159, European Patent No. 0760092, and U.S. Pat. No. 5,783,826, which are all hereby incorporated by reference in their entireties). For example, sensors are mechanically displaced along a vertically positioned measuring cell (or vice versa), and the measurement values are collected at discrete locations in a temporarily successive fashion.

Because the measurements with scanning sensor systems are process-technically contingent, an instantaneous representation of the concentration profile or the local structure of the dispersion over the entire height of the measurement cell is not provided. Scanning times of more than 20 seconds are typical, and a repetition of the measurement is possible, at the earliest, after twice the scanning time. The analysis of the kinetics of rapid separations or of other locally dependent structural changes of dispersions therewith is not possible. With scanning sensor systems, the relative and absolute local resolution is predetermined by the mechanical construction principle (e.g., step width). Resolutions of a few micrometers come with a disproportionate increase of technical and financial expenditure.

In addition, with scanning sensor systems, microvibrations influencing the kinetics of separation phenomena are not completely excluded with mechanical principle solutions having moving sensors or measurement cells.

Moreover, the above-mentioned methods are directed to vertical, cylinder-shaped measurement cells having a circular diameter, the inexact positioning thereof being a frequent source of errors. In addition, with methods based on gravitational force, high measurement times, under certain conditions of months, have to be taken into account for dispersions of higher stability. A process-imminent quality control is thereby impractical.

SUMMARY OF THE INVENTION

The present invention is directed to methods and devices for the classification of separation phenomena.

Exemplary embodiments provide for the classification and quantitative characterization of slow, as well as rapid separation phenomena of disperse material systems of different volume concentration. The stability or instability of a dispersion can be detected, or stabilizing or destabilizing influences on a dispersion can be examined, respectively.

Exemplary embodiments can provide for instantaneous, local and temporal high-resolution detection of the local composition of the dispersion over an entire height of a measurement cell, as well as the temporal change thereof in a short interval (for example, on the order of a hundredth of a second, or less), without movement of the measurement cell, transmitter or receiver. Exemplary embodiments can accommodate a differing volume concentration of the measurement sample and the corresponding target of analysis by using measurement cells having various geometrical dimensions, without further modifications of the device.

By tilting the measurement cell and the transmitter/receiver without a mutual position change, exemplary embodiments permit the separation velocity to be accelerated without the influence of additional mechanical forces, due, for example, to induction of different micro-flow pattern within the dispersion by inclination, and the analysis duration, (for example, for dispersions of higher stability), can thereby be shortened by a multiple, allowing for process-imminent quality controls.

In accordance with exemplary embodiments, methodically relevant data, as well as all original signals, as well as all manually or automatically realized evaluations, can be memorized in a data base and visualized on a monitor or output in any desired form (e.g., a hard copy produced by software). Specific program modules can be provided for the automatic methodical adaptation of the analyzer to the analyte, as well as for a direct process control through optical, acoustical or electronic signals.

Exemplary embodiments are applicable with features from known elements relating to any or all of the products to be measured, measurement cells, wave-emitting sources, and wave-receiving sensors, and can provide instantaneous shots over an entire height of the measurement cell at various azimuthal angles, despite changes of the micro-flow in the dispersion, and without additional power application. Exemplary combinations can achieve a synergetic effect in determining the stability and separation of disperse material systems.

Exemplary embodiments can focus on qualitative and quantitative direct estimation/identification of separation processes of disperse material systems (e.g., liquid-solid, liquid-liquid or liquid-gaseous) with a highest time and local resolution. Exemplary embodiments are also constituted by a variation of the micro-flow in the product to be measured, and therewith, an additional gradual acceleration of the analysis process can be performed without applying external power (e.g., centrifugation) which can be desirable with, for example, gel-stabilized dispersions.

Exemplary embodiments of the present invention are directed to a method and a device for determining the stability and separation of disperse material systems, using tubular measurement cells and wave-emitting sources and wave-receiving sensors. A software-controlled means can be provided which contains measurement cells of optional diameter for receiving a product to be measured. For the detection of local and temporal changes of the composition of the product to be measured, one or more wave-emitting sources and wave-receiving sensors can be provided, which are stationary relative to a position of the respective measurement cell. These can be arranged in such a way that the intensity distribution of the waves/radiation exiting from the sample, is detected locally and temporally over an entire height (or any desired portion) of the measurement cell. Exemplary embodiments allow for the position change of the cell and of the sources and sensors relative to the vertical force of gravitation, without changing their mutual positions.

Exemplary embodiments can include electromagnetic as well as acoustic sources and corresponding sensors, as well as means which can expand an outputted point radiation to a height (or desired portion) of the measurement cell, and align (e.g., parallel) the radiation perpendicular to the longitudinal axis of the measurement cell. The sources and sensors in particular can be configured line-shaped, or any desired shape.

Exemplary measurement cells are comprised of various materials having circular, prismatic or rectangular cross-sections, which can be varied along the longitudinal axis of the measurement cell. By means of a specific structure, several measurement cells can be analyzed independent of one another.

For an exemplary multi-channel variant, several identical measurement modules can be controlled by software, and the device can include, for the multi-channel variant, corresponding means controlled by the software, such as mirrors, plane-parallel transparent plates, an illumination unit and/or a detector unit allowing a synchronous or asynchronous analysis of the various measurement cells to be carried out.

Exemplary embodiments can include add-on contrivances, by which:

feed of an individual measurement cell support with measurement cells can ensue asynchronously (e.g., manually or by means of a robot);

the measurement cells, controlled by software, can be in situ cleaned and repeatedly filled by appropriate means similar to U.S. Pat. Nos. 4,457,624 or 4,099,871, the disclosures of which are hereby incorporated by reference in their entireties, and a sample material in each case can be analyzed;

the measurement cells can be internally thermostated (e.g., connection to a circulation) and controlled by software, cleaned and repeatedly filled, and the sample material in each case can be analyzed;

means (such as racks) can be provided for inclining a measurement module including the measurement cell, a radiation source and a sensor relative to a vertical axis; the inclining means can include manual means (e.g., crank) or, software control of, for example, a stepper motor.

Furthermore, exemplary embodiments can comprise sensors for measuring actual deviation from a vertical, the measured values of which can be polled by software and stored in a database, and fixed separate from the measurement module.

Exemplary heating and/or cooling elements, and temperature sensors for a directed temperature stabilization or for a modification of the temperature of the sample material can be included, as well as redispersion tools integrated for a homogenization before the measurement is started.

Exemplary embodiments of the entire system can also be configured as a mobile measurement device.

In accordance with exemplary embodiments, qualitative and quantitative direct estimation or identification of separation processes of disperse material systems can be achieved. Exemplary embodiments are suitable for use in, for example, the field of development, selection and optimization of destabilizers, stabilizers and novel formulations for dispersions, as well as in quality and process control. Moreover, exemplary embodiments are suitable, for example, in the process technology for separation and treatment processes and in the chemical, pharmaceutical, biotechnological, cosmetic and/or food industries.

BRIEF DESCRIPTION OF THE DRAWINGS

Other objects and advantages of the present invention will become more apparent to those skilled in the art upon reading the detailed description of the preferred embodiments, wherein like elements have been designated by like numerals, and wherein.

DETAILED DESCRIPTION OF THE PREFERRED EMBODIMENT

Figure 1A:
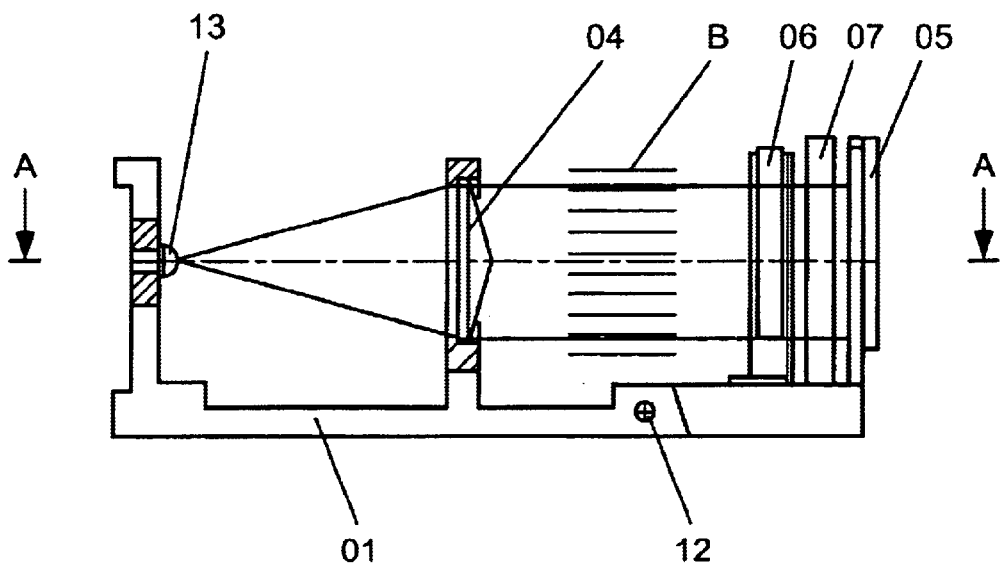
FIGS. 1A–1B show a configuration of a measuring desk according to an exemplary embodiment of the present invention.
Figure 1B:
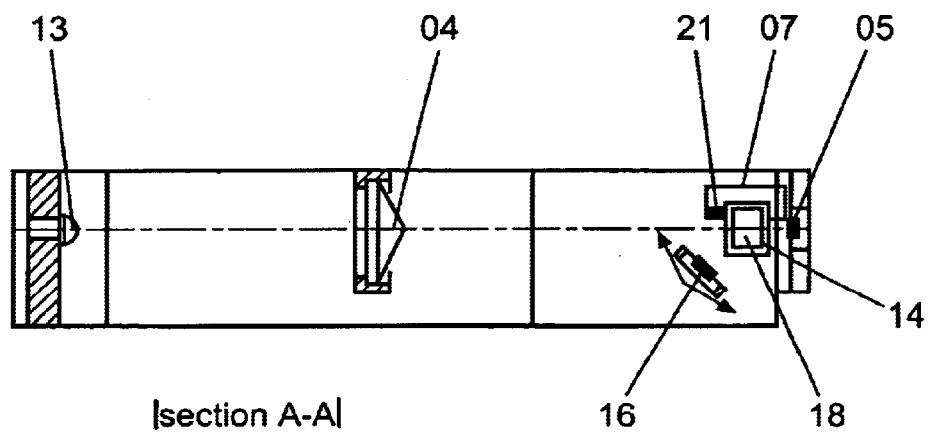

FIGS. 1A and 1B show a measuring desk, represented as a measurement module (12) having a solid frame (01), with a horizontal axis of rotation (02), wherein a radiation source or sources (03), measurement cell support (07) for receiving various types of measurement cells, as well as one or more receivers (e.g., line sensors) (05, 06) are accommodated. A longitudinal axis of the measurement cell(s), source and receiver lines are in one plane. When a monochromatic electromagnetic point radiation source is used, a convex lens (04), a semicylinder, a lens system having corresponding shutters, or any other suitable lens system can be provided for generating parallel optical paths in a viewing plane perpendicular to a measurement cell axis. According to an exemplary embodiment, receiver (05) (e.g., a line sensor) can be positioned as close as possible to the measurement cell, and disposed in parallel to the measurement cell. In addition, a receiver (06), or plural receivers, can be disposed azimuthally parallel to the measurement cell for detecting waves scattered at the particles of the dispersion.

An exemplary method of operation is such that without any refitting whatsoever, various measurement cell geometries having different optical path lengths can be employed. For example, short optical path lengths of a few millimeters, or of any desired, suitable length, can be used for transmission measurements. Longer optical path lengths can, for example, be used for the evaluation of turbidity parameters and/or backscattering analysis.

Feeding of the individual measurement cell supports with measurement cells can ensue manually, automatically, and/or can be done synchronously or asynchronously. For example, in a multichannel embodiment, each of the multiple channels can be fed with samples at approximately the same point in time, and then all of the samples can be measured synchronously (e.g., all of the samples can be measured at common intervals which are synchronized). Alternately, each of the individual samples can be asynchronously measured at the time it is received by a respective measurement cell. According to an exemplary embodiment, the measurement cell can be configured with a discontinuous or continuous feeding with a product to be measured (08), and in-line measurements can be performed.

According to exemplary embodiments, a local resolution of the measurement system for spatial measurement of a sample results from the geometrical dimensions of the individual sensors arranged in the line-shaped configured receiver. For example, charge coupled devices (CCD lines) can be used, characterized by pixel spacings of several micrometers or any other suitable spacing. The information acquired amount can thus be reduced to a minimum without a loss of information content.

For kinetic examinations or any desired examinations, pulsed sources can be used. The temporal resolution of the analysis can be determined as a function of the pulse frequency and the characteristic sensor curve. Measurement intervals in the range of 0.01 seconds, or any other suitable intervals, can be used.

According to exemplary embodiments, a manual or automated mechanical apparatus (e.g. stepper motor (09), a crank (11) and driver (10)) can be used to tilt the entire measurement module (12) relative to the vector of gravity (FIG. 2), without any mutual displacement of the individual parts relative to each other. According to an exemplary embodiment, micro-flow conditions in the separating dispersion can be modified in a directed manner such that the separation in the tilted measurement cell (13) is accelerated as compared to a vertically positioned measurement cell (14) (in parallel to gravity) without application of power (such as, for example, centrifugation). The acceleration can be selected by the realized tilting angle from factor 1 up to plural multiples thereof in accordance with the separation kinetics of the dispersion.

In an exemplary embodiment, laser diodes of the near infrared (e.g., near infrared light emitting diodes, NIR LED) having wavelengths in a range of 850 and 900 nm can be used, the light of which is scattered by the particles in the dispersion in concentration-dependence (in the case of black particles, it can even be absorbed). Singular and/or plural monochromatic sources of other wavelengths, as well as polychromatic sources, can also be used.

Instead of a point source, acoustical or optical line sources having a sufficiently small exit angle or integrally cast lenses can likewise be used for parallelization. In exemplary embodiments, optical systems (e.g., lens (04) of FIG. 1) for collimating the radiation, can be dispensed with.

The collimation of the radiation impinging on the measurement cell or the receiver line, and the accuracy of the representation of areas having a modified concentration, can be increased by, for example, arranging fine bladed diaphragms (e.g., blades B of FIG. 1A) stationarily, in any suitable manner readily apparent to those skilled in the art, perpendicular to a longitudinal axis of the measurement cell and in parallel to a cross-section of the measurement cell.

According to exemplary embodiments, and in addition to the locally described and temporally resolved recording of the concentration and structural changes, along the entire measurement cell at selected points, further sensors or sensor pairs (e.g., for conductivity, pH value, or ion-sensitive electrodes) can be used for determining further substance parameters of the dispersion. Electromagnetic and/or acoustical sources and sensors can also be used, in addition to the optical detection already described, to obtain additional data regarding the samples (e.g., acoustic measurements can be used to measure a density of a given sample).

Exemplary embodiments can be configured such that by means of one or several radiation sources, any number (e.g., 2 through 6 or more) of measurement samples can be examined simultaneously. Optionally, measurement cells having a circular or rectangular cross-section and differing optical path lengths can be used. Thereby, for each measurement sample, the same or an individual test certificate can be selected with respect to measurement cells, measurement frequency, duration of the measurement, radiation intensity or tilting angle.

Figure 3:
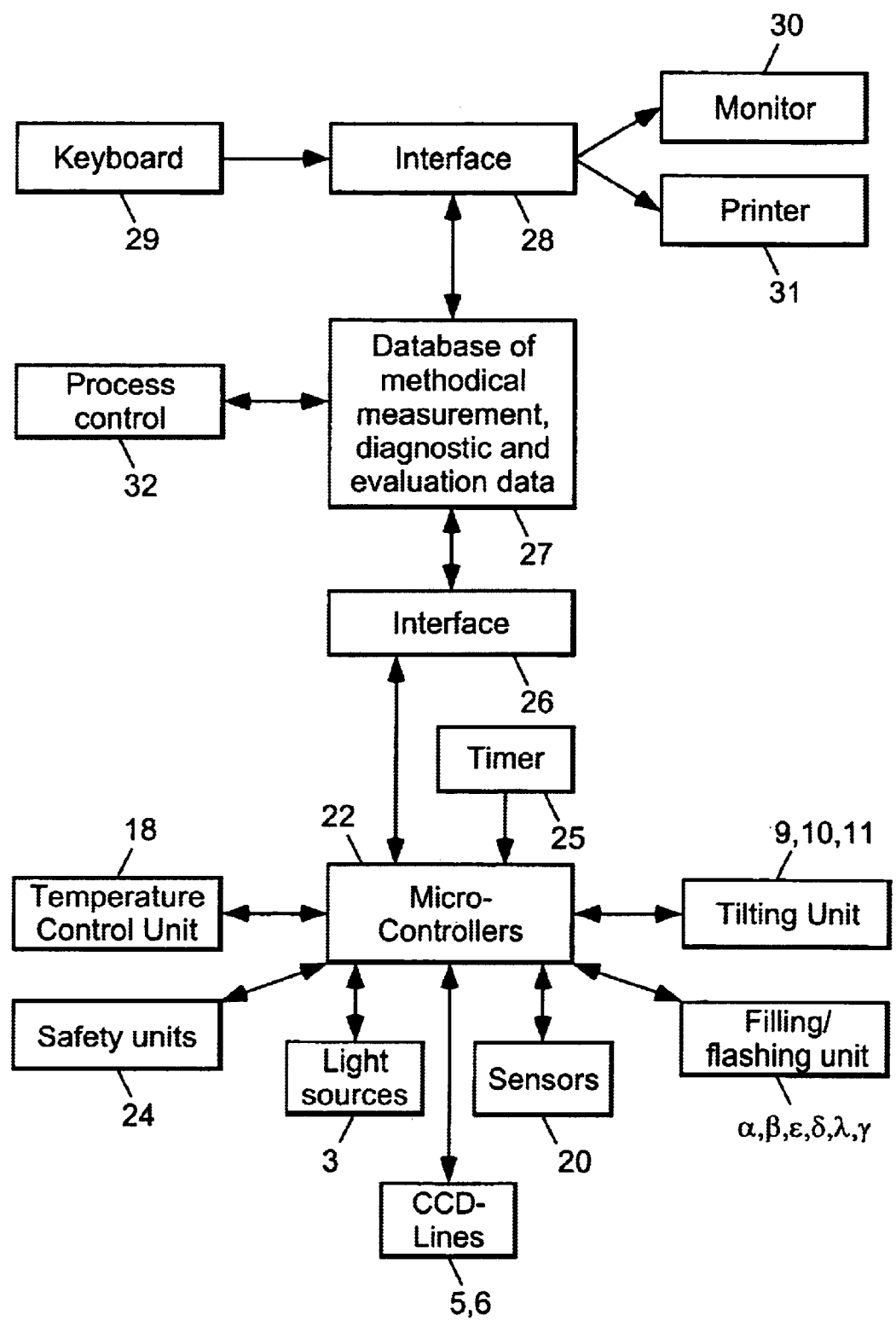
FIG. 3 shows a functional block diagram of the FIG. 2 embodiment of the present invention.

FIG. 3 shows an exemplary functional block diagram a measurement operation which can be performed and automatically optimized on one or multiple measurement cells.

For example, a method of the present invention can be based on using interactive software, to control technically relevant measurement parameters such as sample names, measurement time intervals, irradiation intensity, tilting angle, type of measurement cells, operator, and so forth. Any portion, or all, of the measurement parameters, including control parameters as well as any parameters associated with detected results, can be stored in a common database according to an exemplary embodiment of the present invention. For example, recorded measured intensity data and process temperature can be acquired and automatically stored in a database. The data can be made immediately available for on-line analyses. Thus, supported by software, intensity profiles can be integrated over an entire height (or any desired portion) of the measurement cell and/or in a sample area put in prior to the measurement process, and from an increase per time unit in relation to the maximum possible modification, the stability or separation parameter can be calculated.

The software enables on-line computed stability and separation parameters to be compared with a predefined reference sample or a reference sample which has been measured within the same measurement process. In case of deviation, on-line alarm functions are activated.

Furthermore, software can be used to compare the actual stability or separation parameters with the parameters of the device specification, and optimize automatically the method parameters with respect to measurement time, measurement accuracy, light intensity, tilting angle and storage space required. For example, if slow changes in the separation are detected over a given time (e.g., over a sequence of measurements made at 10 second intervals), the system can automatically increase the interval over which measurements are obtained (e.g., automatically conduct measurements at every hour versus every 10 second interval). Regarding measurement accuracy, if for example, at a given tilting angle (and/or given tilt acceleration), a relatively fast process occurs which results in decreased accuracy of the measurement, the system can automatically reduce the tilting angle, thereby decreasing speed of sedimentation and increasing the accuracy with which measurements can be made (i.e., the system can automatically adapt sedimentation velocity to achieve a desired measurement accuracy). As an additional example, light intensity can be modified by monitoring the output of an optical detector. For example, if a CCD line of detectors receives only a minimum threshold of detected light energy passing from a source through the sample, the intensity of the source can be increased (e.g., increase current fed through an LED) to achieve a desired transmission through the measurement cell. Of course, reductions in light intensity can be similarly controlled automatically. Thus, in exemplary embodiments, an actual radiation intensity distribution can be spatially measured along an entire height of a measurement cell, by instantaneous shots over the entire height, at plural angles (e.g., plural azimuth angles) and can be temporally measured simultaneously or at delayed time intervals.

Exemplary embodiments also include heating and/or cooling elements, and associated temperature sensors, for automatically controlling and stabilizing a temperature of the sample material(s). Temperature control can be achieved by internally thermostatting the measurement cell(s) as discussed, or can be achieved by controlling temperature within the housing using externally thermostatting the measurement cell(s). For example, the FIG. 1 measuring desk can be included in a housing (16) which contains heating and/or cooling elements (18) controlled in response to temperature sensor (20) outputs and an associated controller (22) for stabilizing the temperature within the housing, and thus, within the measurement cell. Alternately, the temperature can be stabilized using heating and/or cooling elements, and associated temperature sensors, for stabilizing temperature of only the measurement cell (e.g., via placement of sensors within the measurement cell).

The measurement cells can be in situ cleaned and/or repeatedly filled, synchronously or asynchronously using any suitable technique. For example, reservoirs can be provided with cleaning fluid, pressurized air and sample material, each of the reservoirs being connected to the measurement cells through suitable conduits and valves (e.g., magnetic valves). A controller can open and close the valves in response to appropriate metering and/or sensor feedback to sequentially clean the measurement cell with cleaning fluid (e.g., until an optical sensor detects a threshold level of transparency of the cleaning fluid as it passes through the measuring cell), to supply pressurized air to the measurement cell (e.g., for a fixed time period or until a sensor, such as a humidity sensor or optical sensor, detects absence of moisture) to dry the cell, to provide a metered refilling of the measurement cell with a new sample, and to analyze the measurement cell (e.g., using electromagnetic and/or mechanical waves parallel and aligned perpendicular relative to a longitudinal axis of a measurement cell). Robotic means can also be used to refill (e.g., replace) the measurement cells.

Redispersion tools (e.g., a vibration device) can be integrated into the measuring desk for homogenization of the sample before it is analyzed. The entire FIG. 1 device can be configured as a self-contained mobile device. Those skilled in the art will appreciate that the measurement cells can be configured in any suitable manner including but not limited to circular, prismatic, rectangular, and/or tubular measurement cells, any of which can be of variable cross section (i.e., a single measurement cell having a variable cross section, or multiple measurement cells wherein each of the measurement cells has a variable cross section).

Sensors can be included for measuring deviations of the measuring desk or any portion thereof from a vertical axis. Measured values can be polled in response to a processor control and stored in the database which can be included within, or external to the measurement module.

Another exemplary feature is that the entire measurement unit, or the measurement cell support can be thermostatted, to standardize the measurement of separation processes. In a software-controlled manner, temperature ramps can be run and, the temperature-dependence of stabilization or destabilization phenomena can be examined. For example, thermostatting can ensue between 100° C. and 60° C. Recording and control of the actual temperature of the product to be measured can ensue by one or more sensor(s) placed in proximity to or within the measurement cell.

Figure 2:
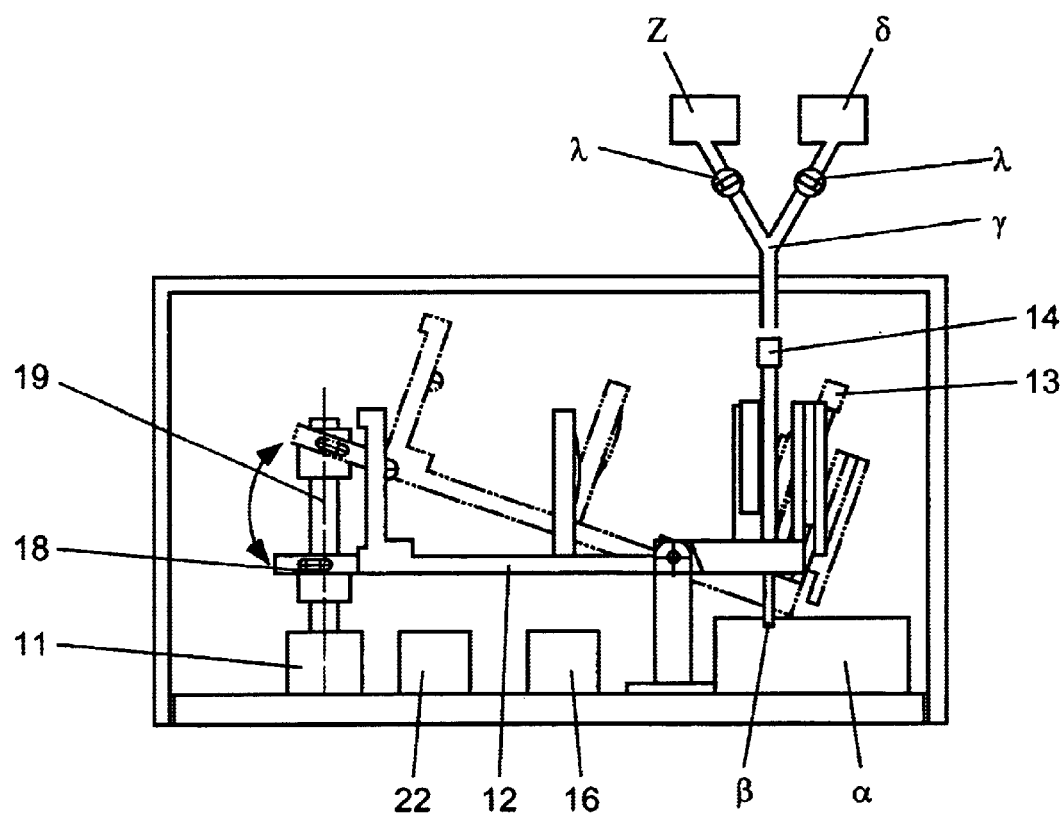
FIG. 2 shows an exemplary tilt operation of the measuring desk.

FIG. 3 shows a functional block diagram of the exemplary embodiment illustrated in FIGS. 1 and 2. In the FIG. 3 embodiment, microcontroller 22 can be any suitable processor such as, but not limited to those available from Intel, Advanced Micro Devices, Philips, or other suitable controller. The microcontroller 22 is shown to receive inputs from CCD lines 5, 6, and sensors, such as temperature sensors 20 as well as any other sensors included in the FIG. 2 measuring desk. The microcontroller supplies control outputs to the light sources 3, tilting unit 9, 10, 11, the temperature control unit 18, and the filling/flashing unit composed of a waste reservoir α for storing a sample and/or cleaning fluid after it has passed through the measuring cell. The microcontoller 22 also controls electronic valves λ, which in turn control a flow of the dispersion to be analyzed from a reservoire and/or a cleaning fluid from a cleaning fluid reservoir δ into the measurement cell via a filling/flashing tube γ.

The microcontrollers also can receive inputs and provide control signals to safety units 24. For example, the safety units 24 can be used to detect when the housing 16 is properly closed, and only enable a measurement analysis upon this condition. Those skilled in the art will appreciate that the safety units can be used to monitor any other conditions and to enable/disable operation of the measuring desk in response thereto.

The FIG. 3 functional block diagram includes an interface 26 between the microcontrollers 22 and a database 27 and associated automated control. The interface 26 can be any suitable interface such as a serial port.

The database 27 can be managed using, for example, a computer represented as interface 28. The computer/interface 28 can receive inputs from a keyboard 29 and provide outputs (e.g., control parameters and/or measurement results) to a monitor 30 and/or printer 31. The computer/interface 28 can use information used in the database to influence an existing process control 32, such as a plant process.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. Device for determining stability and separation of disperse material systems, comprising:
    a measurement cell for receiving a product to be measured;
    a wave-emitting source; and
    a wave-receiving sensor, said source and sensor being arranged relative to a position of the measurement cell so an intensity distribution of waves exiting from a sample to be measured is detected spatially and temporally over an entire height of the measurement cell, the device providing for a modification of a mutual position of the measurement cell and the source and sensor relative to vertical gravitation.

2. Device according to claim 1, comprising:
    a tubular measurement cell of variable cross-section;
    a controller for controlling detection of local and temporal changes in a composition of the product to be measured;
    the wave-emitting source and wave-receiving sensor being arranged stationary relative to a position of the measurement cell; and
    electromagnetic and acoustical sources and sensors.

3. Device according to claim 1, comprising:
    means for expanding an output point of radiation to the height of the measurement cell, and for collimating and aligning said radiation perpendicular to a longitudinal axis of the measurement cell; and
    wherein said source and sensor are a line-shaped source and sensor.

4. Device according to claim 1, comprising:
    bladed diaphragms disposed stationary and perpendicular to a longitudinal axis of the measurement cell and in parallel to a cross-section of the measurement cell.

5. Device according to claim 1, comprising:
    plural measurement cells of various materials having circular, prismatic or rectangular cross-sections which vary along the longitudinal axis of the measurement cell.

6. Device according to claim 1 comprising:
    plural measurement cells which can be analyzed independently of each other.

7. Device according to claim 1, comprising:
    multiple channels controlled by software, and having plural identical measurement modules.

8. Device according to claim 1, comprising:
    at least one of a mirror, plane-parallel transparent plate, an illumination unit and/or a detector unit for analyzing diverse measurement cells.

9. Device according to claim 1, comprising:
    means for feeding an individual measurement cell support with measurement cells asynchronously either manually or by a robot.

10. Device according to claim 1, comprising:
    means, controlled by a software, for in situ cleaning the measurement cells and for repeatedly filling the measurement cells; and
    analyzing sample material in each case.

11. Device according to claim 1, comprising:
    means by which the measurement cells are connected to a circulation; and
    software for cleaning and refill are cleaned and repeatedly filled, and the sample material is in each case analyzed.

12. Device according to claim 1, comprising:
    means for inclining a measurement module including the measurement cell, the source and the sensor relative to a vertical axis, manually by at least one of a crank and a stepper motor.

13. Device according to claim 12, comprising:
    sensors for measuring a deviation from the vertical axis, measured values of which are polled by software and stored in a database, and fixed separate from the measurement module.

14. Device according to claim 1, comprising:
    heating and/or cooling elements; and
    temperature sensors for a directed temperature stabilization or for a modification of the temperature of sample material.

15. Device according to claim 1, comprising:
    redispersion tools integrated for a homogenization before a measurement is started.

16. Device according to claim 1 configured as a mobile measurement device.

17. Method for analyzing disperse material systems in a measurement cell using a wave-emitting source and wave-receiving sensor comprising the steps of:
    spatially analyzing local changes in composition, due to separation phenomena, of a dispersion present in a measurement cell over an entire height of the measurement cell, using a wave-emitting source and a wave-receiving sensor which are stationary relative to the measurement cell; and
    modifying a micro-flow of the dispersion by modification of a position of the measurement cell and sources and sensors relative to a vertical gravitation without a mutual change of position of the measurement cell, wave-emitting source and wave-receiving sensor.

18. Method according to claim 17, comprising:

configuring electromagnetic or mechanical waves parallel and aligned perpendicular relative to a longitudinal axis of the measurement cell.

19. Method according to claim 17, comprising:

using differing wavelengths during one measurement procedure.

20. Method according to claim 17, comprising:

emitting waves from the source in a pulsed manner.

21. Method according to claims 17, comprising:

measuring actual radiation intensity distribution along the measurement cell at plural azimuthal angles and, simultaneously or delayed, at determined time intervals.

22. Method according to claim 17, comprising:

tilting a measurement module which contains measurement cell relative to a vertical alignment thereof; and accelerating the measurement cell at different degrees.

23. Method according to claim 17, comprising:

introducing additional variable sensors into the measurement cell for determining substance parameters of the dispersion during separation.

24. Method according to claim 17, comprising:

standardization or for assessment of temperature-dependence of stabilizing or destabilizing phenomena, temperature preset during measurement.

25. Method according to claim 17, comprising:

performing stability analyses with individual test certificates simultaneously for plural dispersion samples.

26. Method according to claim 17, comprising:

feeding of individual measurement cell support with measurement cells at least one of manually, automatically, synchronously and asynchronously.

27. Method according to claim 17, comprising:

feeding the measurement cell continuously with a product to be measured for in-line measurements.

28. Method according to claim 17, comprising:

automatically storing technically relevant measurement parameters including at least one of sample names, measurement time intervals, irradiation intensity, tilting angle, type of measurement cells, operator identification recorded measured intensity data and process temperature in a base; and providing the stored parameters for on-line analyses.

29. Method according to claim 17, comprising:

integrating intensity profiles for a sample area put in prior to a measurement process, and from an increase per time unit in relation to a maximum modification, calculating at least one of a stability and separation parameter.

30. Method according to claim 17, comprising:

comparing at least one of an on-line calculated stability or separation parameter with at least one of a predefined reference sample and a reference sample measured in the same measurement process; and activating or placing at the disposal of the process control, on-line alarm functions upon deviations.

31. Method according to claim 17, comprising:

comparing the actual stability and separation parameters with parameters of a device specification, and automatically optimizing the parameters with respect to measurement time, measurement accuracy, light intensity, tilting angle and storage space required.

32. Method according to claim 17, comprising:

using the device as a mobile measurement device.

33. Method according to claim 17, comprising:

providing a qualitative and quantitative direct estimation/identification of separation processes of disperse material systems.

34. Method according to claim 33, comprising:

determining the stability and separation in at least one of a field of development, selection and optimization of destabilizers, stabilizers and novel formulations for dispersions, and in quality and process control.

35. Method according to claim 33 comprising:

using the method in process technology for separation and treatment processes.

36. Method according to claim 33 comprising:

using the method in at least one of chemical, pharmaceutical, biotechnological, cosmetic and food industries.

37. Device according to claim 1, wherein the sample is detected over the entire height of the measurement cell by instantaneous shots.

38. Method according to claim 17, comprising:

accelerating the separation phenomena to shorten a stability analysis of the disperse material.

* * * * *